US012576263B2

(12) United States Patent
Baumbach et al.

(10) Patent No.: US 12,576,263 B2
(45) Date of Patent: Mar. 17, 2026

(54) DEVICE FOR ATTACHING A HEART SUPPORT SYSTEM TO AN INSERTION DEVICE, AND METHOD FOR PRODUCING SAME

(71) Applicant: KARDION GMBH, Stuttgart (DE)

(72) Inventors: Hardy Baumbach, Stuttgart (DE); Inga Schellenberg, Stuttgart (DE); David Minzenmay, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 1024 days.

(21) Appl. No.: 17/057,045

(22) PCT Filed: May 30, 2019

(86) PCT No.: PCT/EP2019/064130
§ 371 (c)(1),
(2) Date: Jun. 1, 2021

(87) PCT Pub. No.: WO2019/229207
PCT Pub. Date: Dec. 5, 2019

(65) Prior Publication Data
US 2021/0290939 A1 Sep. 23, 2021

(30) Foreign Application Priority Data
May 30, 2018 (DE) .......................... 102018208537.4

(51) Int. Cl.
*A61M 60/861* (2021.01)
*A61M 60/178* (2021.01)
(Continued)

(52) U.S. Cl.
CPC ........ *A61M 60/861* (2021.01); *A61M 60/178* (2021.01); *A61M 60/857* (2021.01); *A61M 60/859* (2021.01); *A61M 60/865* (2021.01)

(58) Field of Classification Search
CPC .......................... A61M 60/861; A61M 60/859
See application file for complete search history.

(56) References Cited

U.S. PATENT DOCUMENTS

| | | | |
|---|---|---|---|
| 3,568,659 A | 3/1971 | Karnegis | |
| 4,522,194 A | 6/1985 | Normann | |
| (Continued) | | | |

FOREIGN PATENT DOCUMENTS

| | | | | |
|---|---|---|---|---|
| CA | 3 000 581 | | 4/2017 | |
| CN | 1524000 A | * | 8/2004 | .......... A61M 1/1058 |
| (Continued) | | | | |

OTHER PUBLICATIONS

International Preliminary Report on Patentability and Written Opinion received in PCT Application No. PCT/EP2019/064130, dated Dec. 10, 2020 in 8 pages.

(Continued)

*Primary Examiner* — Unsu Jung
*Assistant Examiner* — Laura Hodge
(74) *Attorney, Agent, or Firm* — Knobbe, Martens, Olson & Bear, LLP

(57) ABSTRACT

The invention relates to an apparatus (100) for attaching a cardiac support system to an insertion device, wherein apparatus (100) is shaped to releasably couple the cardiac support system to the insertion device. The apparatus (100) has at least one main body (105), in particular a tubular main body (115), and a clamping device (110) with at least one clamping wing (115). The clamping device (110) is designed to mechanically couple the cardiac support system to the insertion device in an attachment state and to release the cardiac support system from the insertion device by displacing and/or flipping open the at least one clamping wing (115) in a release state.

20 Claims, 5 Drawing Sheets

(51) Int. Cl.
    *A61M 60/857*     (2021.01)
    *A61M 60/859*     (2021.01)
    *A61M 60/865*     (2021.01)

(56)           References Cited

U.S. PATENT DOCUMENTS

| | | | |
|---|---|---|---|
| 4,802,650 A | 2/1989 | Stricker | |
| 4,902,272 A | 2/1990 | Milder et al. | |
| 4,919,647 A | 4/1990 | Nash | |
| 4,921,479 A | 5/1990 | Grayzel | |
| 4,943,275 A | 7/1990 | Stricker | |
| 4,968,300 A | 11/1990 | Moutafis et al. | |
| 4,985,014 A | 1/1991 | Orejola | |
| 5,061,256 A | 10/1991 | Wampler | |
| 5,084,064 A | 1/1992 | Barak et al. | |
| 5,090,957 A | 2/1992 | Moutafis et al. | |
| 5,112,292 A | 5/1992 | Hwang et al. | |
| 5,116,305 A | 5/1992 | Milder et al. | |
| 5,322,509 A | 6/1994 | Rickerd | |
| 5,330,460 A | 7/1994 | Moss et al. | |
| 5,354,271 A | 10/1994 | Voda | |
| 5,409,463 A | 4/1995 | Thomas et al. | |
| 5,647,127 A | 7/1997 | Miyata et al. | |
| 5,752,937 A | 5/1998 | Otten et al. | |
| 5,921,913 A | 7/1999 | Siess | |
| 5,928,132 A | 7/1999 | Leschinsky | |
| 6,152,909 A | 11/2000 | Bagaoisan | |
| 6,159,198 A | 12/2000 | Gardeski et al. | |
| 6,176,848 B1 | 1/2001 | Rau et al. | |
| 6,450,948 B1 | 9/2002 | Matsuura et al. | |
| 6,497,681 B1 | 12/2002 | Brenner | |
| 6,530,876 B1 | 3/2003 | Spence | |
| 6,544,247 B1 | 4/2003 | Gardeski et al. | |
| 6,743,239 B1 * | 6/2004 | Kuehn | A61B 17/1285 |
| | | | 600/101 |
| 6,794,789 B2 | 9/2004 | Siess et al. | |
| 6,879,126 B2 | 4/2005 | Paden et al. | |
| 7,022,100 B1 | 4/2006 | Aboul-Hosn et al. | |
| 7,166,088 B2 | 1/2007 | Heuser | |
| 7,241,257 B1 | 7/2007 | Ainsworth et al. | |
| 7,250,041 B2 | 7/2007 | Chiu et al. | |
| 7,357,794 B2 | 4/2008 | Makower et al. | |
| 7,419,486 B2 | 9/2008 | Kampa | |
| 7,621,894 B2 | 11/2009 | Leeflang et al. | |
| 7,722,568 B2 | 5/2010 | Lenker et al. | |
| 7,744,571 B2 | 6/2010 | Fisher et al. | |
| 7,824,375 B2 | 11/2010 | Hastings, Jr. et al. | |
| 7,841,976 B2 | 11/2010 | McBride et al. | |
| 7,878,967 B1 | 2/2011 | Khanal | |
| 7,951,119 B2 | 5/2011 | Leeflang et al. | |
| 8,012,079 B2 | 9/2011 | Delgado, III | |
| 8,025,647 B2 | 9/2011 | Siess et al. | |
| 8,043,263 B2 | 10/2011 | Helgeson et al. | |
| 8,088,154 B2 | 1/2012 | Hoffman et al. | |
| 8,152,845 B2 | 4/2012 | Bourque | |
| 8,157,719 B1 | 4/2012 | Ainsworth et al. | |
| 8,231,519 B2 | 7/2012 | Reichenbach et al. | |
| 8,262,619 B2 | 9/2012 | Chebator et al. | |
| 8,292,908 B2 | 10/2012 | Nieman et al. | |
| 8,343,028 B2 | 1/2013 | Gregoric et al. | |
| 8,382,830 B2 | 2/2013 | Maher et al. | |
| 8,475,431 B2 | 7/2013 | Howat | |
| 8,480,627 B2 | 7/2013 | Christiansen | |
| 8,485,961 B2 | 7/2013 | Campbell et al. | |
| 8,545,380 B2 | 10/2013 | Farnan et al. | |
| 8,579,966 B2 | 11/2013 | Seguin et al. | |
| 8,591,538 B2 | 11/2013 | Gellman | |
| 8,591,539 B2 | 11/2013 | Gellman | |
| 8,597,170 B2 | 12/2013 | Walters et al. | |
| 8,613,777 B2 | 12/2013 | Siess et al. | |
| 8,684,904 B2 | 4/2014 | Campbell et al. | |
| 8,721,517 B2 | 5/2014 | Zeng et al. | |
| 8,727,959 B2 | 5/2014 | Reitan et al. | |
| 8,728,055 B2 | 5/2014 | Stehr et al. | |
| 8,734,331 B2 | 5/2014 | Evans et al. | |
| 8,814,776 B2 | 8/2014 | Hastie et al. | |
| 8,852,173 B2 | 10/2014 | Sigg et al. | |
| 8,888,728 B2 | 11/2014 | Aboul-Hosn et al. | |
| 8,900,115 B2 | 12/2014 | Bolling et al. | |
| 8,926,564 B2 | 1/2015 | King et al. | |
| 8,932,246 B2 | 1/2015 | Ferrari | |
| 8,992,406 B2 | 3/2015 | Corbett | |
| 9,138,518 B2 | 9/2015 | Campbell et al. | |
| 9,144,669 B2 | 9/2015 | Wieselthaler | |
| 9,149,606 B2 | 10/2015 | Beissel et al. | |
| 9,162,017 B2 | 10/2015 | Evans et al. | |
| 9,168,060 B2 | 10/2015 | Voss | |
| 9,308,305 B2 | 4/2016 | Chen et al. | |
| 9,327,068 B2 | 5/2016 | Aboul-Hosn et al. | |
| 9,364,592 B2 | 6/2016 | McBride | |
| 9,402,942 B2 | 8/2016 | Hastie et al. | |
| 9,452,249 B2 | 9/2016 | Kearsley et al. | |
| 9,486,566 B2 | 11/2016 | Siess | |
| 9,510,813 B2 | 12/2016 | Levy et al. | |
| 9,539,094 B2 | 1/2017 | Dale et al. | |
| 9,539,378 B2 | 1/2017 | Tuseth | |
| 9,545,468 B2 | 1/2017 | Aboul-Hosn et al. | |
| 9,561,314 B2 | 2/2017 | Aboul-Hosn et al. | |
| 9,569,985 B2 | 2/2017 | Alkhatib et al. | |
| 9,585,991 B2 | 3/2017 | Spence | |
| 9,597,063 B2 | 3/2017 | Voss et al. | |
| 9,616,159 B2 | 4/2017 | Anderson et al. | |
| 9,656,011 B2 | 5/2017 | Graham et al. | |
| 9,669,144 B2 | 6/2017 | Spanier et al. | |
| 9,682,180 B2 | 6/2017 | Hoarau et al. | |
| 9,724,083 B2 | 8/2017 | Quadri et al. | |
| 9,744,279 B2 | 8/2017 | Tamez et al. | |
| 9,750,861 B2 | 9/2017 | Hastie et al. | |
| 9,769,912 B2 | 9/2017 | Helm et al. | |
| 9,782,905 B2 | 10/2017 | Drake et al. | |
| 9,789,238 B2 | 10/2017 | Aboul-Hosn et al. | |
| 9,807,860 B2 | 10/2017 | Helm et al. | |
| 9,814,813 B2 | 11/2017 | Corbett | |
| 9,814,814 B2 | 11/2017 | Corbett et al. | |
| 9,821,101 B2 | 11/2017 | Andrus et al. | |
| 9,821,146 B2 | 11/2017 | Tao et al. | |
| 9,827,356 B2 | 11/2017 | Muller et al. | |
| 9,872,948 B2 | 1/2018 | Siess | |
| 9,974,893 B2 | 5/2018 | Toellner | |
| 9,974,938 B2 | 5/2018 | Pepin et al. | |
| 9,999,714 B2 | 6/2018 | Spanier et al. | |
| 10,010,412 B2 | 7/2018 | Taft | |
| 10,080,871 B2 | 9/2018 | Schumacher et al. | |
| 10,123,875 B2 | 11/2018 | Wildhirt et al. | |
| 10,183,104 B2 | 1/2019 | Anderson et al. | |
| 10,207,037 B2 | 2/2019 | Corbett et al. | |
| 10,207,038 B2 | 2/2019 | Neumann | |
| 10,238,782 B2 | 3/2019 | Barry | |
| 10,238,783 B2 | 3/2019 | Aboul-Hosn et al. | |
| 10,258,771 B2 | 4/2019 | Beissel et al. | |
| 10,279,093 B2 | 5/2019 | Reichenbach et al. | |
| 10,300,185 B2 | 5/2019 | Aboul-Hosn et al. | |
| 10,300,249 B2 | 5/2019 | Tao et al. | |
| 10,350,384 B2 | 7/2019 | Farnan et al. | |
| 10,357,598 B2 | 7/2019 | Aboul-Hosn et al. | |
| 10,376,162 B2 | 8/2019 | Edelman et al. | |
| 10,441,771 B2 | 10/2019 | Bickhart et al. | |
| 10,449,279 B2 | 10/2019 | Muller | |
| 10,478,542 B2 | 11/2019 | Jahangir | |
| 10,493,191 B2 | 12/2019 | Whisenant et al. | |
| 10,537,431 B2 | 1/2020 | Zhou et al. | |
| 10,537,672 B2 | 1/2020 | Tuseth et al. | |
| 10,576,192 B2 | 3/2020 | Muller et al. | |
| 10,576,258 B2 | 3/2020 | Fantuzzi et al. | |
| 10,617,808 B2 | 4/2020 | Hastie et al. | |
| 10,709,828 B2 | 7/2020 | Toellner et al. | |
| 10,737,008 B2 | 8/2020 | Corbett et al. | |
| 10,737,086 B2 | 8/2020 | Agrawal et al. | |
| 10,806,904 B2 | 10/2020 | Jelle et al. | |
| 10,857,274 B2 | 12/2020 | Alexander et al. | |
| 10,864,015 B2 | 12/2020 | Von Segesser | |
| 10,864,308 B2 | 12/2020 | Muller et al. | |
| 10,881,836 B2 | 1/2021 | Schumacher et al. | |
| 10,881,845 B2 | 1/2021 | Siess et al. | |

(56)  References Cited

U.S. PATENT DOCUMENTS

| | | | |
|---|---|---|---|
| 10,894,143 | B2 | 1/2021 | Yokoyama |
| 10,898,625 | B2 | 1/2021 | Toellner |
| 10,953,205 | B2 | 3/2021 | Korkuch |
| 10,959,878 | B2 | 3/2021 | Wolfertz et al. |
| 10,967,152 | B2 | 4/2021 | Korkuch |
| 11,007,350 | B2 | 5/2021 | Tao et al. |
| 11,045,624 | B2 | 6/2021 | Oiwa |
| 11,045,634 | B2 | 6/2021 | Korkuch et al. |
| 11,058,851 | B2 | 7/2021 | Farnan |
| 11,065,417 | B2 | 7/2021 | Inukai et al. |
| 11,076,884 | B2 | 8/2021 | Anderson et al. |
| 11,090,465 | B2 | 8/2021 | Weber et al. |
| 11,096,568 | B2 | 8/2021 | Harrah et al. |
| 11,129,959 | B2 | 9/2021 | Hart et al. |
| 11,129,969 | B2 | 9/2021 | Pederson, Jr. et al. |
| 11,173,295 | B2 | 11/2021 | Mack et al. |
| 11,191,927 | B2 | 12/2021 | McLaughlin et al. |
| 11,197,690 | B2 | 12/2021 | Fantuzzi et al. |
| 11,219,755 | B2 | 1/2022 | Siess et al. |
| 11,241,312 | B2 | 2/2022 | Simonin |
| 11,266,502 | B1 | 3/2022 | Wallace |
| 11,291,800 | B2 | 4/2022 | Yokota |
| 11,291,805 | B2 | 4/2022 | Ouchi et al. |
| 11,291,821 | B2 | 4/2022 | Agrawal et al. |
| 11,291,855 | B2 | 4/2022 | Wiesener |
| 11,304,747 | B2 | 4/2022 | Simani et al. |
| 11,304,755 | B2 | 4/2022 | Cao et al. |
| 11,311,311 | B2 | 4/2022 | Sperry et al. |
| 11,318,284 | B2 | 5/2022 | Ishida et al. |
| 11,318,285 | B2 | 5/2022 | Ishida |
| 11,318,290 | B2 | 5/2022 | Kleinhaus |
| 11,324,920 | B2 | 5/2022 | Inukai et al. |
| 11,331,082 | B2 | 5/2022 | Itoh et al. |
| 11,331,450 | B2 | 5/2022 | Sakaguchi |
| 11,331,451 | B2 | 5/2022 | Yamashita et al. |
| 11,351,359 | B2 | 6/2022 | Clifton et al. |
| 11,364,363 | B2 | 6/2022 | Fantuzzi et al. |
| 11,369,413 | B2 | 6/2022 | Murphy |
| 11,377,512 | B2 | 7/2022 | Kuramoto et al. |
| 11,389,633 | B2 | 7/2022 | Rohl et al. |
| 11,400,261 | B2 | 8/2022 | Mathews et al. |
| 11,406,395 | B2 | 8/2022 | Wada et al. |
| 11,406,522 | B2 | 8/2022 | Folan et al. |
| 11,406,798 | B2 | 8/2022 | Kambara |
| 11,406,799 | B2 | 8/2022 | McEvaddy et al. |
| 11,413,446 | B2 | 8/2022 | Siess et al. |
| 11,419,721 | B2 | 8/2022 | Poppe et al. |
| 11,419,743 | B2 | 8/2022 | Poppe et al. |
| 11,426,562 | B2 | 8/2022 | Fantuzzi |
| 11,439,791 | B2 | 9/2022 | Ishida |
| 11,446,044 | B2 | 9/2022 | Bonnette et al. |
| 11,446,414 | B2 | 9/2022 | Oiwa |
| 11,452,575 | B2 | 9/2022 | Morey et al. |
| 11,458,285 | B2 | 10/2022 | Graham et al. |
| 11,471,026 | B2 | 10/2022 | Piskun et al. |
| 11,471,663 | B2 | 10/2022 | Tuval et al. |
| 11,471,665 | B2 | 10/2022 | Clifton et al. |
| 11,484,698 | B2 | 11/2022 | Radman |
| 11,497,889 | B2 | 11/2022 | Mixter et al. |
| 11,497,894 | B2 | 11/2022 | Korkuch et al. |
| 11,497,896 | B2 | 11/2022 | Tanner et al. |
| 11,503,993 | B2 | 11/2022 | Chu et al. |
| 11,504,102 | B2 | 11/2022 | Stanton et al. |
| 11,511,083 | B2 | 11/2022 | Wada |
| 11,511,084 | B2 | 11/2022 | Chu |
| 11,511,098 | B2 | 11/2022 | Agrawal et al. |
| 11,511,101 | B2 | 11/2022 | Hastie et al. |
| 11,517,191 | B2 | 12/2022 | Oskin |
| 11,517,720 | B2 | 12/2022 | Korkuch et al. |
| 11,517,738 | B2 | 12/2022 | Wisniewski |
| 11,523,905 | B2 | 12/2022 | Griswold et al. |
| 11,524,137 | B2 | 12/2022 | Jahangir |
| 11,524,153 | B2 | 12/2022 | Alexander et al. |
| 11,529,510 | B2 | 12/2022 | Leven |
| 11,540,857 | B2 | 1/2023 | Olson et al. |
| 11,564,710 | B2 | 1/2023 | Fitterer et al. |
| 11,565,093 | B2 | 1/2023 | Kirt et al. |
| 11,583,670 | B2 | 2/2023 | Pfeifer et al. |
| 11,602,448 | B2 | 3/2023 | Nygaard et al. |
| 11,628,280 | B2 | 4/2023 | Schumacher et al. |
| 11,633,574 | B2 | 4/2023 | Watanabe |
| 11,642,511 | B2 | 5/2023 | Delgado, III |
| 11,660,434 | B2 | 5/2023 | Korkuch et al. |
| 11,679,250 | B2 | 6/2023 | Alexander et al. |
| 11,690,606 | B2 | 7/2023 | Muller et al. |
| 11,690,979 | B2 | 7/2023 | Voss et al. |
| 11,690,997 | B2 | 7/2023 | Georges et al. |
| 11,697,002 | B2 | 7/2023 | Korkuch |
| 11,730,939 | B2 | 8/2023 | Siess et al. |
| 11,730,942 | B2 | 8/2023 | Fantuzzi et al. |
| D998,799 | S | 9/2023 | Okamura et al. |
| 11,744,567 | B2 | 9/2023 | Deuel et al. |
| 11,744,638 | B2 | 9/2023 | Davies et al. |
| 11,751,751 | B2 | 9/2023 | Calabrese et al. |
| 11,751,753 | B2 | 9/2023 | Levasseur et al. |
| 11,752,308 | B2 | 9/2023 | Tao et al. |
| 11,759,610 | B2 | 9/2023 | Calabrese et al. |
| 11,766,264 | B2 | 9/2023 | Phan et al. |
| 11,766,555 | B2 | 9/2023 | Matthes et al. |
| 11,771,444 | B2 | 10/2023 | Crawford et al. |
| 11,779,194 | B2 | 10/2023 | Wilder et al. |
| 11,779,338 | B2 | 10/2023 | Gordon et al. |
| 11,779,361 | B2 | 10/2023 | Kugler et al. |
| 11,779,729 | B2 | 10/2023 | Guimaraes et al. |
| 11,779,743 | B2 | 10/2023 | Agrawal et al. |
| 11,786,109 | B2 | 10/2023 | Golden et al. |
| 11,786,701 | B2 | 10/2023 | Maki et al. |
| 11,786,720 | B2 | 10/2023 | Muller |
| 11,793,530 | B2 | 10/2023 | Chu et al. |
| 11,793,977 | B2 | 10/2023 | Korkuch et al. |
| 11,806,046 | B2 | 11/2023 | Fantuzzi et al. |
| 11,806,116 | B2 | 11/2023 | Tuval et al. |
| 11,806,117 | B2 | 11/2023 | Tuval et al. |
| 11,806,258 | B2 | 11/2023 | Hingston et al. |
| 11,812,944 | B2 | 11/2023 | Wales et al. |
| 11,812,951 | B2 | 11/2023 | Mitelberg et al. |
| 11,812,952 | B2 | 11/2023 | Abbott et al. |
| 11,813,183 | B2 | 11/2023 | Christakis et al. |
| 11,813,445 | B2 | 11/2023 | Alexander et al. |
| 11,826,517 | B2 | 11/2023 | Fuller et al. |
| 11,832,793 | B2 | 12/2023 | McWeeney et al. |
| 11,832,868 | B2 | 12/2023 | Smail et al. |
| 11,833,314 | B2 | 12/2023 | Corbett et al. |
| 11,833,316 | B2 | 12/2023 | Hayakawa et al. |
| 11,833,342 | B2 | 12/2023 | Tanner et al. |
| 11,844,592 | B2 | 12/2023 | Tuval et al. |
| 11,844,909 | B2 | 12/2023 | Tassoni et al. |
| 11,844,940 | B2 | 12/2023 | D'Ambrosio et al. |
| 11,850,373 | B2 | 12/2023 | Golden et al. |
| 11,857,159 | B2 | 1/2024 | Saenz Villalobos et al. |
| 11,857,161 | B2 | 1/2024 | Nguyen et al. |
| 11,857,197 | B2 | 1/2024 | Alexander et al. |
| 11,857,740 | B2 | 1/2024 | Chu |
| 11,857,743 | B2 | 1/2024 | Fantuzzi et al. |
| 11,864,746 | B2 | 1/2024 | Melilli et al. |
| 11,865,275 | B2 | 1/2024 | O'Carrol et al. |
| 11,871,962 | B2 | 1/2024 | Tehrani et al. |
| 11,877,753 | B2 | 1/2024 | Connolly et al. |
| 11,878,131 | B2 | 1/2024 | Pedersen et al. |
| 11,883,062 | B2 | 1/2024 | Rawson |
| 11,883,274 | B2 | 1/2024 | Schwammenthal et al. |
| D1,015,536 | S | 2/2024 | Walsh |
| 11,890,085 | B2 | 2/2024 | Duval et al. |
| 11,890,428 | B2 | 2/2024 | Ito |
| 11,890,435 | B2 | 2/2024 | Takagi |
| 11,896,474 | B2 | 2/2024 | Hynes et al. |
| 11,896,482 | B2 | 2/2024 | Delaloye et al. |
| 11,896,814 | B2 | 2/2024 | Shambaugh, Jr. |
| 11,903,589 | B2 | 2/2024 | Stahman et al. |
| 11,903,600 | B2 | 2/2024 | Chu et al. |
| 11,903,831 | B2 | 2/2024 | Shuey et al. |
| 11,903,857 | B2 | 2/2024 | Folan |
| 11,911,072 | B2 | 2/2024 | Fantuzzi et al. |
| 11,911,305 | B2 | 2/2024 | Smith et al. |

(56) References Cited

U.S. PATENT DOCUMENTS

| | | | |
|---|---|---|---|
| 11,918,186 B2 | 3/2024 | Chu et al. | |
| 11,918,187 B2 | 3/2024 | Cahill et al. | |
| 11,918,202 B2 | 3/2024 | Deuel et al. | |
| 11,918,219 B2 | 3/2024 | Smith et al. | |
| 11,918,470 B2 | 3/2024 | Jarral et al. | |
| 11,918,752 B2 | 3/2024 | Tassoni et al. | |
| 11,918,764 B2 | 3/2024 | Soltis et al. | |
| 11,918,780 B2 | 3/2024 | Jagelski et al. | |
| 11,925,315 B2 | 3/2024 | Chu et al. | |
| 11,925,383 B2 | 3/2024 | Tada et al. | |
| 11,925,386 B2 | 3/2024 | Favreau | |
| 11,925,795 B2 | 3/2024 | Muller et al. | |
| 11,930,996 B2 | 3/2024 | Dresher | |
| 11,930,997 B2 | 3/2024 | Melito et al. | |
| 11,931,003 B2 | 3/2024 | Congdon et al. | |
| 11,931,058 B2 | 3/2024 | Spangler et al. | |
| 11,931,068 B2 | 3/2024 | Fitterer et al. | |
| 11,931,073 B2 | 3/2024 | Walsh et al. | |
| 11,931,098 B2 | 3/2024 | Moriyama | |
| 11,931,278 B2 | 3/2024 | Wood et al. | |
| 11,931,528 B2 | 3/2024 | Rohl et al. | |
| 11,931,530 B2 | 3/2024 | Campbell et al. | |
| 11,937,774 B2 | 3/2024 | Wood et al. | |
| 11,937,871 B2 | 3/2024 | Crawford et al. | |
| 11,938,047 B2 | 3/2024 | Christakis et al. | |
| 11,938,285 B2 | 3/2024 | Lau et al. | |
| D1,028,246 S | 5/2024 | Delorenzo | |
| 11,986,602 B2 | 5/2024 | Corbett | |
| 11,986,604 B2 | 5/2024 | Siess | |
| 12,017,076 B2 | 6/2024 | Tan et al. | |
| 12,023,476 B2 | 7/2024 | Tuval et al. | |
| 12,023,477 B2 | 7/2024 | Siess | |
| 12,059,559 B2 | 8/2024 | Muller et al. | |
| 12,064,614 B2 | 8/2024 | Agah et al. | |
| 12,076,497 B2 | 9/2024 | Fantuzzi et al. | |
| 12,121,681 B2 | 10/2024 | Korkuch | |
| 12,138,438 B2 | 11/2024 | Alexander et al. | |
| 12,161,855 B2 | 12/2024 | Hastie et al. | |
| 12,161,857 B2 | 12/2024 | Saul et al. | |
| 12,186,517 B2 | 1/2025 | Modlish et al. | |
| 12,233,224 B2 | 2/2025 | Korkuch et al. | |
| 12,239,799 B2 | 3/2025 | Corbett et al. | |
| 12,263,330 B2 | 4/2025 | D'Ambrosio et al. | |
| 12,268,860 B1 | 4/2025 | Fishman et al. | |
| 12,290,673 B2 | 5/2025 | Jahangir | |
| 12,296,134 B2 | 5/2025 | Siess et al. | |
| 12,318,560 B2 | 6/2025 | O'Carrol et al. | |
| 12,337,163 B2 | 6/2025 | Radman | |
| 12,343,516 B2 | 7/2025 | Cook | |
| 12,357,801 B2 | 7/2025 | Korkuch et al. | |
| 12,369,944 B2 | 7/2025 | Fantuzzi et al. | |
| 12,370,357 B2 | 7/2025 | Corbett et al. | |
| D1,090,825 S | 8/2025 | Loughlin et al. | |
| D1,090,829 S | 8/2025 | Loughlin et al. | |
| 12,397,146 B2 | 8/2025 | Hart et al. | |
| 12,402,910 B2 | 9/2025 | Korkuch | |
| 12,403,287 B2 | 9/2025 | Tao et al. | |
| 12,403,296 B2 | 9/2025 | Baumbach et al. | |
| 12,409,299 B2 | 9/2025 | Fantuzzi et al. | |
| 12,440,663 B2 | 10/2025 | Tuval et al. | |
| 12,447,309 B2 | 10/2025 | Siess et al. | |
| 12,447,316 B2 | 10/2025 | Voss et al. | |
| 12,453,848 B2 | 10/2025 | Tuval et al. | |
| 12,458,792 B2 | 11/2025 | Zarins | |
| 2002/0052638 A1 | 5/2002 | Zadno-Azizi | |
| 2002/0077600 A1 | 6/2002 | Sirimanne | |
| 2002/0107482 A1 | 8/2002 | Rocamora et al. | |
| 2003/0032941 A1 | 2/2003 | Boyle et al. | |
| 2004/0034411 A1 | 2/2004 | Quijano | |
| 2004/0044266 A1 | 3/2004 | Siess et al. | |
| 2004/0102674 A1 | 5/2004 | Zadini et al. | |
| 2005/0182435 A1 | 8/2005 | Andrews et al. | |
| 2005/0272975 A1 | 12/2005 | McWeeney | |
| 2006/0155158 A1 | 7/2006 | Aboul-Hosn | |
| 2006/0224110 A1 | 10/2006 | Scott et al. | |
| 2008/0086027 A1 | 4/2008 | Siess et al. | |
| 2008/0097293 A1 | 4/2008 | Chin et al. | |
| 2008/0097386 A1 | 4/2008 | Osypka | |
| 2008/0114339 A1 | 5/2008 | McBride et al. | |
| 2008/0183136 A1 | 7/2008 | Lenker et al. | |
| 2008/0269822 A1 | 10/2008 | Ljungstrom et al. | |
| 2009/0054840 A1 | 2/2009 | Drake et al. | |
| 2009/0069886 A1 | 3/2009 | Suri et al. | |
| 2009/0182200 A1 | 7/2009 | Golden | |
| 2009/0203957 A1 | 8/2009 | LaRose et al. | |
| 2011/0034874 A1 | 2/2011 | Reitan | |
| 2011/0124962 A1* | 5/2011 | Gordin | A61B 17/29 |
| | | | 600/104 |
| 2011/0230821 A1 | 9/2011 | Babic | |
| 2011/0282274 A1 | 11/2011 | Fulton, III | |
| 2012/0029265 A1 | 2/2012 | LaRose | |
| 2012/0035645 A1 | 2/2012 | Gross | |
| 2012/0221021 A1* | 8/2012 | Hoarau | A61B 17/072 |
| | | | 606/151 |
| 2012/0296313 A1 | 11/2012 | Andreacchi et al. | |
| 2013/0085318 A1 | 4/2013 | Toellner | |
| 2013/0211324 A1 | 8/2013 | Voss et al. | |
| 2013/0303831 A1* | 11/2013 | Evans | A61M 60/865 |
| | | | 600/16 |
| 2013/0303970 A1 | 11/2013 | Keenan et al. | |
| 2014/0005467 A1 | 1/2014 | Farnan et al. | |
| 2014/0180250 A1 | 6/2014 | Belson | |
| 2015/0045696 A1 | 2/2015 | Osypka | |
| 2015/0066082 A1* | 3/2015 | Moshe | A61B 17/0401 |
| | | | 606/232 |
| 2015/0090372 A1 | 4/2015 | Branagan et al. | |
| 2015/0119633 A1 | 4/2015 | Haselby et al. | |
| 2015/0141738 A1 | 5/2015 | Toellner et al. | |
| 2015/0151087 A1 | 6/2015 | Suzuki et al. | |
| 2015/0290372 A1 | 10/2015 | Muller et al. | |
| 2015/0290432 A1 | 10/2015 | Mathews et al. | |
| 2015/0306291 A1 | 10/2015 | Bonde et al. | |
| 2015/0343179 A1 | 12/2015 | Schumacher et al. | |
| 2015/0359952 A1* | 12/2015 | Andrus | A61M 60/861 |
| | | | 600/16 |
| 2016/0095744 A1 | 4/2016 | Wolfertz et al. | |
| 2016/0256620 A1 | 9/2016 | Scheckel et al. | |
| 2016/0271309 A1 | 9/2016 | Throckmorton et al. | |
| 2017/0043074 A1 | 2/2017 | Siess | |
| 2017/0065267 A1 | 3/2017 | Fantuzzi et al. | |
| 2017/0080199 A1 | 3/2017 | Murphy | |
| 2017/0143938 A1 | 5/2017 | Ogle et al. | |
| 2017/0209099 A1 | 7/2017 | Caron et al. | |
| 2017/0215918 A1 | 8/2017 | Tao et al. | |
| 2017/0232169 A1 | 8/2017 | Muller | |
| 2017/0232170 A1 | 8/2017 | Jarvik | |
| 2017/0232171 A1 | 8/2017 | Roehn et al. | |
| 2017/0312492 A1 | 11/2017 | Fantuzzi et al. | |
| 2017/0368245 A1 | 12/2017 | Kantrowitz et al. | |
| 2018/0001003 A1 | 1/2018 | Moran et al. | |
| 2018/0015214 A1 | 1/2018 | Lynch | |
| 2018/0093070 A1* | 4/2018 | Cottone | A61M 25/0041 |
| 2018/0099076 A1 | 4/2018 | LaRose | |
| 2018/0099078 A1 | 4/2018 | Tuseth et al. | |
| 2018/0104397 A1 | 4/2018 | Schumacher | |
| 2018/0200422 A1 | 7/2018 | Nguyen et al. | |
| 2018/0207334 A1 | 7/2018 | Siess | |
| 2018/0243004 A1 | 8/2018 | von Segesser et al. | |
| 2018/0296742 A1 | 10/2018 | Toellner | |
| 2018/0303990 A1 | 10/2018 | Siess et al. | |
| 2018/0318547 A1 | 11/2018 | Yokoyama | |
| 2018/0326131 A1 | 11/2018 | Muller et al. | |
| 2018/0344987 A1 | 12/2018 | Lancette et al. | |
| 2019/0001103 A1 | 1/2019 | Korkuch | |
| 2019/0015232 A1 | 1/2019 | Tuseth et al. | |
| 2019/0015568 A1 | 1/2019 | Tuseth | |
| 2019/0015570 A1 | 1/2019 | Muller | |
| 2019/0060543 A1 | 2/2019 | Khanal et al. | |
| 2019/0069898 A1 | 3/2019 | Farnan | |
| 2019/0076167 A1 | 3/2019 | Fantuzzi et al. | |
| 2019/0083082 A1 | 3/2019 | Tassoni, Jr. et al. | |
| 2019/0083690 A1 | 3/2019 | Siess et al. | |
| 2019/0167122 A1 | 6/2019 | Obermiller et al. | |
| 2019/0167305 A1 | 6/2019 | Pedersen et al. | |

(56) References Cited

U.S. PATENT DOCUMENTS

| | | |
|---|---|---|
| 2019/0184078 A1 | 6/2019 | Zilbershlag et al. |
| 2019/0223877 A1 | 7/2019 | Nitzen et al. |
| 2019/0224390 A1 | 7/2019 | Barry |
| 2019/0231523 A1 | 8/2019 | Lombardi |
| 2019/0232025 A1 | 8/2019 | Tao et al. |
| 2019/0247627 A1 | 8/2019 | Korkuch et al. |
| 2019/0282741 A1 | 9/2019 | Franano et al. |
| 2019/0290817 A1 | 9/2019 | Guo et al. |
| 2019/0298974 A1 | 10/2019 | Siess et al. |
| 2019/0321527 A1 | 10/2019 | King et al. |
| 2019/0344000 A1 | 11/2019 | Kushwaha et al. |
| 2019/0344052 A1 | 11/2019 | Klepetko |
| 2019/0365975 A1 | 12/2019 | Muller et al. |
| 2019/0381226 A1 | 12/2019 | Morozov et al. |
| 2020/0000988 A1 | 1/2020 | Epple |
| 2020/0000989 A1 | 1/2020 | Matheis et al. |
| 2020/0022811 A1 | 1/2020 | Griswold |
| 2020/0023109 A1 | 1/2020 | Epple |
| 2020/0023110 A1 | 1/2020 | Jahangir |
| 2020/0023113 A1 | 1/2020 | Epple et al. |
| 2020/0054857 A1 | 2/2020 | Scheckel |
| 2020/0054861 A1 | 2/2020 | Korkuch et al. |
| 2020/0086021 A1 | 3/2020 | Jeevanandam et al. |
| 2020/0094019 A1 | 3/2020 | Siess et al. |
| 2020/0121905 A1 | 4/2020 | Zoll |
| 2020/0129684 A1 | 4/2020 | Pfeffer et al. |
| 2020/0139028 A1 | 5/2020 | Scheckel et al. |
| 2020/0147283 A1 | 5/2020 | Tanner et al. |
| 2020/0155739 A1 | 5/2020 | Siess et al. |
| 2020/0164125 A1 | 5/2020 | Muller et al. |
| 2020/0179657 A1 | 6/2020 | Liu |
| 2020/0261633 A1 | 8/2020 | Spanier |
| 2020/0345337 A1 | 11/2020 | Muller et al. |
| 2021/0093836 A1 | 4/2021 | Fantuzzi |
| 2021/0146116 A1 | 5/2021 | Siess |
| 2021/0205585 A1 | 7/2021 | Ullmann |
| 2021/0275791 A1 | 9/2021 | Korkuch et al. |
| 2021/0290931 A1 | 9/2021 | Baumbach |
| 2021/0379352 A1 | 12/2021 | Schlebusch et al. |
| 2022/0008053 A1 | 1/2022 | Fitzgerald et al. |
| 2022/0096125 A1 | 3/2022 | Fantuzzi et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0339400 A1 | 10/2022 | Fantuzzi et al. |
| 2023/0091199 A1 | 3/2023 | Siess et al. |
| 2023/0145482 A1 | 5/2023 | Garrigue |
| 2023/0233834 A1 | 7/2023 | Alexander et al. |
| 2023/0277833 A1 | 9/2023 | Sharma et al. |
| 2023/0293878 A1 | 9/2023 | Christof et al. |
| 2023/0398330 A1 | 12/2023 | Mitze et al. |
| 2023/0405286 A1 | 12/2023 | Schumacher et al. |
| 2024/0074828 A1 | 3/2024 | Wenning |
| 2024/0165392 A1 | 5/2024 | Liu et al. |
| 2024/0269451 A1 | 8/2024 | Siess et al. |
| 2025/0082922 A1 | 3/2025 | Fabiunke et al. |
| 2025/0134652 A1 | 5/2025 | Maiorano |

FOREIGN PATENT DOCUMENTS

| | | | | |
|---|---|---|---|---|
| CN | 102438552 A | * | 5/2012 | ....... A61B 17/00234 |
| CN | 204106671 | | 1/2015 | |
| CN | 106512117 | | 3/2017 | |
| CN | 107080871 | | 8/2017 | |
| CN | 206443963 | | 8/2017 | |
| CN | 107206139 A | * | 9/2017 | .......... A61F 2/2478 |
| CN | 107412892 | | 12/2017 | |
| CN | 207708250 | | 8/2018 | |
| CN | 106902404 | | 8/2019 | |
| CN | 110237327 | | 9/2019 | |
| CN | 209790495 | | 12/2019 | |
| CN | 110665079 | | 1/2020 | |
| CN | 112168427 | | 1/2021 | |
| CN | 113413544 | | 9/2021 | |
| CN | 215691046 | | 2/2022 | |
| CN | 114886614 | | 8/2022 | |
| CN | 115916111 | | 4/2023 | |
| CN | 218922664 | | 4/2023 | |
| CN | 116271502 | | 6/2023 | |
| CN | 116688321 | | 10/2023 | |
| CN | 117959584 | | 5/2024 | |
| CN | 118717356 | | 10/2024 | |
| CN | 119033506 | | 11/2024 | |
| DE | 10 2009 011 726 | | 9/2010 | |
| DE | 10 2009 047 845 | | 3/2011 | |
| DE | 11 2009 000 185 | | 3/2013 | |
| DE | 20 2013 007 408 | | 12/2014 | |
| DE | 10 2014 212 323 | | 12/2015 | |
| DE | 10 2016 122 268 | | 5/2018 | |
| DE | 10 2018 208 537 | | 12/2019 | |
| DE | 10 2018 208 564 | | 12/2019 | |
| DE | 10 2018 211 297 | | 1/2020 | |
| EP | 0 064 212 | | 11/1982 | |
| EP | 0 411 605 | | 2/1991 | |
| EP | 0 629 412 | | 12/1994 | |
| EP | 0 898 481 | | 1/2002 | |
| EP | 1 105 181 | | 2/2004 | |
| EP | 1 660 164 | | 4/2009 | |
| EP | 2 039 390 | | 11/2010 | |
| EP | 2 436 417 | | 4/2012 | |
| EP | 2 716 242 | | 4/2014 | |
| EP | 2 015 821 | | 5/2015 | |
| EP | 2 519 273 | | 8/2015 | |
| EP | 2 680 896 | | 1/2016 | |
| EP | 2 475 415 | | 6/2016 | |
| EP | 2 934 649 | | 11/2016 | |
| EP | 2 646 068 | | 3/2017 | |
| EP | 3187222 A1 | * | 7/2017 | ........ A61M 25/0026 |
| EP | 3 398 625 | | 11/2018 | |
| EP | 3 131 599 | | 2/2019 | |
| EP | 3 508 245 | | 7/2019 | |
| EP | 3 528 865 | | 8/2019 | |
| EP | 3 187 222 | | 9/2019 | |
| EP | 3 077 038 | | 10/2019 | |
| EP | 2 962 720 | | 1/2020 | |
| EP | 1 819 391 | | 2/2020 | |
| EP | 3 189 862 | | 2/2020 | |
| EP | 3 618 886 | | 3/2020 | |
| EP | 2 922 593 | | 4/2020 | |
| EP | 3 180 064 | | 4/2020 | |
| EP | 3 687 625 | | 8/2020 | |
| EP | 3 131 597 | | 12/2020 | |
| EP | 3 419 711 | | 3/2021 | |
| EP | 4 271 461 | | 3/2021 | |
| EP | 3 131 615 | | 6/2021 | |
| EP | 3 323 465 | | 7/2021 | |
| EP | 3 570 926 | | 7/2021 | |
| EP | 3 851 151 | | 7/2021 | |
| EP | 3 247 440 | | 8/2021 | |
| EP | 3 656 293 | | 8/2021 | |
| EP | 3 006 072 | | 9/2021 | |
| EP | 3 351 209 | | 10/2021 | |
| EP | 3 592 411 | | 11/2021 | |
| EP | 3 618 884 | | 11/2021 | |
| EP | 3 914 330 | | 12/2021 | |
| EP | 3 337 530 | | 3/2022 | |
| EP | 2 967 630 | | 4/2022 | |
| EP | 3 755 237 | | 4/2022 | |
| EP | 3 978 060 | | 4/2022 | |
| EP | 3 153 205 | | 5/2022 | |
| EP | 3 407 811 | | 5/2022 | |
| EP | 3 124 071 | | 6/2022 | |
| EP | 3 636 312 | | 6/2022 | |
| EP | 3 661 436 | | 6/2022 | |
| EP | 3 231 395 | | 8/2022 | |
| EP | 4 039 320 | | 8/2022 | |
| EP | 3 487 550 | | 9/2022 | |
| EP | 3 756 721 | | 9/2022 | |
| EP | 3 834 876 | | 9/2022 | |
| EP | 3 849 646 | | 10/2022 | |
| EP | 3 000 493 | | 11/2022 | |
| EP | 3 028 736 | | 11/2022 | |
| EP | 3 077 035 | | 11/2022 | |
| EP | 3 305 357 | | 11/2022 | |

(56)             References Cited

FOREIGN PATENT DOCUMENTS

| | | |
|---|---|---|
| EP | 3 389 530 | 11/2022 |
| EP | 3 570 762 | 11/2022 |
| EP | 3 579 905 | 11/2022 |
| EP | 3 858 422 | 11/2022 |
| EP | 3 866 876 | 11/2022 |
| EP | 3 199 198 | 12/2022 |
| EP | 3 270 999 | 12/2022 |
| EP | 3 398 562 | 12/2022 |
| EP | 3 402 562 | 12/2022 |
| EP | 3 538 173 | 3/2023 |
| EP | 3 551 271 | 7/2023 |
| EP | 3 692 933 | 9/2023 |
| EP | 3 713 634 | 9/2023 |
| EP | 3 773 130 | 9/2023 |
| EP | 3 895 638 | 9/2023 |
| EP | 3 903 701 | 9/2023 |
| EP | 3 178 515 | 10/2023 |
| EP | 3 253 302 | 10/2023 |
| EP | 3 603 727 | 10/2023 |
| EP | 3 773 129 | 10/2023 |
| EP | 3 777 952 | 10/2023 |
| EP | 4 052 754 | 10/2023 |
| EP | 4 149 606 | 10/2023 |
| EP | 3 515 525 | 11/2023 |
| EP | 3 583 927 | 11/2023 |
| EP | 3 744 362 | 11/2023 |
| EP | 3 766 428 | 11/2023 |
| EP | 3 773 363 | 11/2023 |
| EP | 3 840 670 | 11/2023 |
| EP | 3 711 698 | 12/2023 |
| EP | 3 752 236 | 12/2023 |
| EP | 3 349 671 | 1/2024 |
| EP | 3 349 839 | 1/2024 |
| EP | 3 443 915 | 1/2024 |
| EP | 3 487 421 | 1/2024 |
| EP | 3 784 305 | 1/2024 |
| EP | 3 925 659 | 1/2024 |
| EP | 3 242 613 | 2/2024 |
| EP | 3 509 504 | 2/2024 |
| EP | 3 518 836 | 2/2024 |
| EP | 3 534 805 | 2/2024 |
| EP | 3 566 636 | 2/2024 |
| EP | 3 603 728 | 2/2024 |
| EP | 3 700 464 | 2/2024 |
| EP | 3 718 588 | 2/2024 |
| EP | 3 768 342 | 2/2024 |
| EP | 3 820 412 | 2/2024 |
| EP | 3 053 532 | 3/2024 |
| EP | 3 142 573 | 3/2024 |
| EP | 3 275 499 | 3/2024 |
| EP | 3 397 147 | 3/2024 |
| EP | 3 424 551 | 3/2024 |
| EP | 3 492 042 | 3/2024 |
| EP | 3 528 885 | 3/2024 |
| EP | 3 563 805 | 3/2024 |
| EP | 3 927 254 | 3/2024 |
| EP | 3 955 796 | 3/2024 |
| EP | 4 037 574 | 3/2024 |
| EP | 4 140 532 | 5/2024 |
| EP | 3 970 765 | 7/2024 |
| EP | 3 789 054 | 8/2024 |
| EP | 3 793 633 | 8/2024 |
| EP | 4 419 042 | 8/2024 |
| EP | 4 429 750 | 9/2024 |
| EP | 3 534 985 | 10/2024 |
| EP | 3 893 957 | 10/2024 |
| EP | 3 641 845 | 11/2024 |
| EP | 3 643 350 | 11/2024 |
| EP | 4 034 221 | 11/2024 |
| EP | 3 522 947 | 2/2025 |
| EP | 4 429 754 | 2/2025 |
| EP | 4 429 751 | 3/2025 |
| EP | 4 429 752 | 3/2025 |
| EP | 4 429 753 | 3/2025 |
| EP | 3 958 921 | 5/2025 |
| EP | 3 463 539 | 6/2025 |
| EP | 4 100 091 | 7/2025 |
| EP | 3 908 177 | 8/2025 |
| EP | 3 706 853 | 10/2025 |
| EP | 4 046 678 | 10/2025 |
| GB | 2 451 161 | 12/2011 |
| GB | 2 545 750 | 6/2017 |
| JP | S59-076463 | 5/1984 |
| JP | H04-176471 | 6/1992 |
| JP | H08-504621 | 5/1996 |
| JP | H09-028664 | 2/1997 |
| JP | 2001-515374 | 9/2001 |
| JP | 6267625 | 1/2018 |
| WO | WO 97/037697 | 10/1997 |
| WO | WO 2005/007024 | 1/2005 |
| WO | WO 2005/028014 | 3/2005 |
| WO | WO 2007/006055 | 1/2007 |
| WO | WO 2007/044510 | 4/2007 |
| WO | WO 2008/106103 | 9/2008 |
| WO | WO 2009/114456 | 9/2009 |
| WO | WO 2010/014418 | 2/2010 |
| WO | WO 2010/092347 | 8/2010 |
| WO | WO 2011/096975 | 8/2011 |
| WO | WO 2011/160858 | 12/2011 |
| WO | WO 2013/013248 | 1/2013 |
| WO | WO 2013/092971 | 6/2013 |
| WO | WO 2013/093058 | 6/2013 |
| WO | WO 2014/096408 | 6/2014 |
| WO | WO 2015/019132 | 2/2015 |
| WO | WO-2015134944 A1 * | 9/2015 .......... A61M 60/216 |
| WO | WO 2016/028644 | 2/2016 |
| WO | WO 2016/055368 | 4/2016 |
| WO | WO 2017/053361 | 3/2017 |
| WO | WO 2017/053988 | 3/2017 |
| WO | WO 2017/060257 | 4/2017 |
| WO | WO 2017/118738 | 7/2017 |
| WO | WO 2017/147103 | 8/2017 |
| WO | WO-2017157884 A1 * | 9/2017 ..... A61B 17/320016 |
| WO | WO-2017194562 A1 * | 11/2017 .......... A61F 2/2409 |
| WO | WO 2018/078615 | 5/2018 |
| WO | WO 2018/081040 | 5/2018 |
| WO | WO 2018/165519 | 9/2018 |
| WO | WO 2018/202779 | 11/2018 |
| WO | WO 2018/234454 | 12/2018 |
| WO | WO 2019/035804 | 2/2019 |
| WO | WO 2019/038343 | 2/2019 |
| WO | WO 2019/038345 | 2/2019 |
| WO | WO 2019/055591 | 3/2019 |
| WO | WO 2019/067233 | 4/2019 |
| WO | WO 2019/118371 | 6/2019 |
| WO | WO 2019/161245 | 8/2019 |
| WO | WO 2019/180181 | 9/2019 |
| WO | WO 2019/191245 | 10/2019 |
| WO | WO 2019/193604 | 10/2019 |
| WO | WO 2019/219883 | 11/2019 |
| WO | WO 2019/229206 | 12/2019 |
| WO | WO 2019/229207 | 12/2019 |
| WO | WO 2019/229223 | 12/2019 |
| WO | WO 2019/229224 | 12/2019 |
| WO | WO 2020/003110 | 1/2020 |
| WO | WO 2020/011760 | 1/2020 |
| WO | WO 2020/123333 | 6/2020 |
| WO | WO 2020/132211 | 6/2020 |
| WO | WO 2020/137708 | 7/2020 |
| WO | WO 2020/219430 | 10/2020 |
| WO | WO 2021/062265 | 4/2021 |
| WO | WO 2021/150777 | 7/2021 |
| WO | WO 2023/040546 | 12/2021 |
| WO | WO 2022/011095 | 1/2022 |
| WO | WO 2022/032286 | 2/2022 |
| WO | WO 2022/091784 | 5/2022 |
| WO | WO 2022/109589 | 5/2022 |
| WO | WO 2022/109591 | 5/2022 |
| WO | WO 2023/003937 | 1/2023 |
| WO | WO 2024/125157 | 5/2023 |
| WO | WO 2023/112044 | 6/2023 |
| WO | WO 2023/230157 | 11/2023 |

(56) References Cited

FOREIGN PATENT DOCUMENTS

| | | |
|---|---|---|
| WO | WO 2024/243154 | 11/2024 |
| WO | WO 2025/075927 | 4/2025 |

OTHER PUBLICATIONS

International Search Report and Written Opinion received in PCT Application No. PCT/EP2019/064130, dated Sep. 12, 2019 in 9 pages.

"Edwards Sapien 3 Kit—Transapical and Transaortic", Edwards Lifesciences, Released Nov. 8, 2016, p. 11. chrome-extension://efaidnbmnnnibpcajpcglclefindmkaj/https://edwardsprod.blob.core.windows.net/media/De/sapien3/doc-0045537b%20-%20certitude.pdf.

Park et al., "A Novel Electrical Potential Sensing Method for in Vitro Stent Fracture Monitoring and Detection", Jan. 1, 2011, vol. 21, No. 4, pp. 213-222.

"Transvalvular Insertion Tool (TVI)", Pressure Products, Feb. 2013, https://www.pressure-products.com/wip/tvi.html, as printed Jul. 25, 2024 in 2 pages.

Gopinath, Divya, "A System for Impedance Characterization of Coronary Stents", University of Strathclyde Engineering, Thesis, Aug. 2015, pp. 77.

Bergersen et al., "Congenital Heart Disease: The Catheterization Manual", Netherlands, Springer, 2009, pp. 115-118 and 143-150.

* cited by examiner

DEVICE FOR ATTACHING A HEART SUPPORT SYSTEM TO AN INSERTION DEVICE, AND METHOD FOR PRODUCING SAME

BACKGROUND

Field

The invention is based on an apparatus or a method of the type of the independent claims. The present invention also relates to a computer program.

Description of the Related Art

A heart valve prosthesis can be inserted using a catheter procedure. The catheter makes it possible to insert, position and release the heart valve prosthesis via a mechanism controlled from the outside by the surgeon. For cardiac support systems for long-term and short-term support, also referred to as VAD systems, other, more invasive surgical techniques, such as sternotomies, are used. Systems for short-term support, such as impella pumps, are implanted without special catheters.

SUMMARY

Based on this, the underlying object of the invention is to specify an apparatus for inserting a cardiac support system and a method for producing said system.

With this in mind, the approach presented here provides an apparatus for attaching a cardiac support system to an insertion device, a method for producing an apparatus for attaching a cardiac support system to an insertion device, a production apparatus that uses this method and lastly a corresponding computer program according to the main claims. Advantageous further developments and improvements of the apparatus specified in the independent claim are possible using the measures specified in the dependent claims.

With the approach presented here, a cardiac support system, also referred to as a ventricular support system or VAD, can be releasably coupled to an insertion device in order to be able to insert the cardiac support system, for example into a body or a vascular system, in a minimally invasive manner. An apparatus securely couples the cardiac support system to be implanted to the insertion device with a releasable clamping device, thus enabling a controlled and targeted insertion of the cardiac support system which can, for example, be pushed into a catheter of the insertion device for this purpose. At the destination, the attachment of the cardiac support system to the insertion device can be released by the apparatus, which allows the cardiac support system to be released in a targeted manner. The apparatus remains coupled to the insertion device and can thus be removed together with the insertion device after the cardiac support system has been released.

An apparatus for attaching a cardiac support system to an insertion device will be presented. The apparatus is configured to releasably couple the cardiac support system to the insertion device. The apparatus comprises at least one main body, in particular a tube-shaped main body, and a clamping device having at least one clamping wing. The clamping device is configured to mechanically couple the cardiac support system to the insertion device in an attachment state. The clamping device is further configured to release the cardiac support system from the insertion device by displacing and/or flipping open the at least one clamping wing in a release state.

The apparatus can be made of an elastic material that simultaneously exhibits a certain degree of stiffness, for example Nitinol. The apparatus can be coupled to the housing of the cardiac support system and to the insertion device, for example via a form-locking connection and/or a frictional connection. It can be implemented as a connecting element, for example, whereby the cardiac support system can be coupled to an end portion of the apparatus, and the insertion device can be coupled to another end portion of the apparatus. To bring about the attachment state, the at least one clamping wing can engage, for example in a form-locking manner, in a connecting element on the housing of the cardiac support system, and the insertion device can, for example, be coupled to the main body of the apparatus. In the release state, the cardiac support system can be released from the apparatus, and thus from the insertion device, by flipping open the at least one clamping wing. The apparatus can remain coupled to the insertion device in the release state, for example in order to be able to remove the apparatus from the body together with the insertion device after the cardiac support system has successfully been released at the destination.

The cardiac support system can, for example, be a right ventricular support system, a left ventricular support system, a biventricular support system or a vascular or valve prosthesis. The apparatus can furthermore also be used to releasably couple another vascular or intracavitary implant, such as a gastrointestinal, intrathecal, or intravesical implant, to the insertion device, in order to guide the respective implant to the destination via the apparatus and be able to release it there. The insertion device can be used as a medical or surgical instrument, for example, and comprise a catheter and/or be at least partly insertable into a catheter. Using the apparatus, it is advantageously possible to insert the cardiac support system in a minimally invasive manner. Minimally invasive insertion can reduce the trauma of a surgical procedure and accelerates convalescence. Since cardiac support systems can be implanted quickly without a catheter, a targeted positioning of the cardiac support system by the surgeon can be difficult. The apparatus presented here advantageously enables a releasable attachment of the cardiac support system to the insertion device, which can advantageously facilitate a controlled and targeted implantation and release of the cardiac support system at the destination.

According to one advantageous embodiment, the at least one clamping wing of the clamping device can be configured as a shape memory element. For this purpose, the clamping wing can be made of a shape memory polymer or a shape memory alloy, for example, preferably Nitinol. The implementation of the at least one clamping wing as a shape memory element, for example made of Nitinol, is particularly advantageous with regard to flipping open the at least one clamping wing in the release state of the clamping device. In the attachment state, the at least one clamping wing can be in a pretensioned state, for example, and, for the release state, return to its original state, the originally embossed basic form, to flip open. In addition to the at least one clamping wing, it is also possible for the clamping device, for example, or the entire apparatus to be configured as a shape memory element.

Furthermore, according to one embodiment, the at least one clamping wing can comprise at least one element which engages or can engage in an end portion of a cardiac support system in a form-locking manner and/or at least one recess for receiving an element for mechanically coupling the cardiac support system to the apparatus in a form-locking manner. The recess and/or the element can be centered in the clamping wing, for example, in order to secure the cardiac support system in a particularly stable manner. The element and the recess can have different shapes; they can have a circular, oval, triangular or polygonal or star shape, for example, and the cross-section of the element can, for example, include a rectangle, a flattened portion, a rounded portion, a semicircle or an undercut. The elements can have a diameter of 1.5 millimeters and a height of 0.5 millimeters, for example. If the clamping wing has only one recess for an element provided on the housing of the cardiac support system, for example, the height of the recess can, for example, correspond to the wall thickness of the clamping wing.

For the stable attachment of the cardiac support system to the apparatus and thus to the insertion device, it can also be advantageous if, according to one embodiment, the clamping device has two clamping wings, in particular whereby the at least two clamping wings (for example on either side) are evenly spaced. The clamping device can, for example, also comprise a plurality of clamping wings, for example three clamping wings, in particular whereby these clamping wings are equal distances apart from one another. This embodiment having at least two clamping wings can be advantageous with respect to the attachment state in terms of a particularly stable fixation of the cardiac support system. It can also be advantageous with respect to the release state of the cardiac support system, in particular when the at least two clamping wings are evenly spaced on either side, so that uniform flipping open of the clamping wings does not change the position of the cardiac support system at the destination when it is released.

BRIEF DESCRIPTION OF THE DRAWINGS

According to one embodiment, the apparatus can additionally comprise a sleeve, whereby the sleeve is configured to enclose the apparatus in the attachment state of the clamping device. The attachment state of the cardiac support system to the apparatus can, for example, be effected by pushing the at least one clamping wing axially over the specially configured housing of the cardiac support system. For this purpose, the housing of the cardiac support system can comprise a form-locking element, for example, or recesses for receiving a form-locking element of the at least one clamping wing according to one embodiment. After the clamping wing is folded down, the sleeve can be guided over the apparatus, for example, which can, for example, be flexible and bendable. The clamping wing can now be held down by the sleeve, for example, and the cardiac support system can be inserted into a catheter, for example in its attachment state, which can be inserted into the circulatory system for implantation of the cardiac support system. Axial and rotational force transmission to the cardiac support system for external control is possible. The attachment can be implemented such that the apparatus can be held securely via the sleeve by a radial force and remain connected to the housing of the cardiac support system. This can be advantageous, because both forward and backward movements can then be carried out during implantation without affecting the connection.

DETAILED DESCRIPTION

Figure 1:
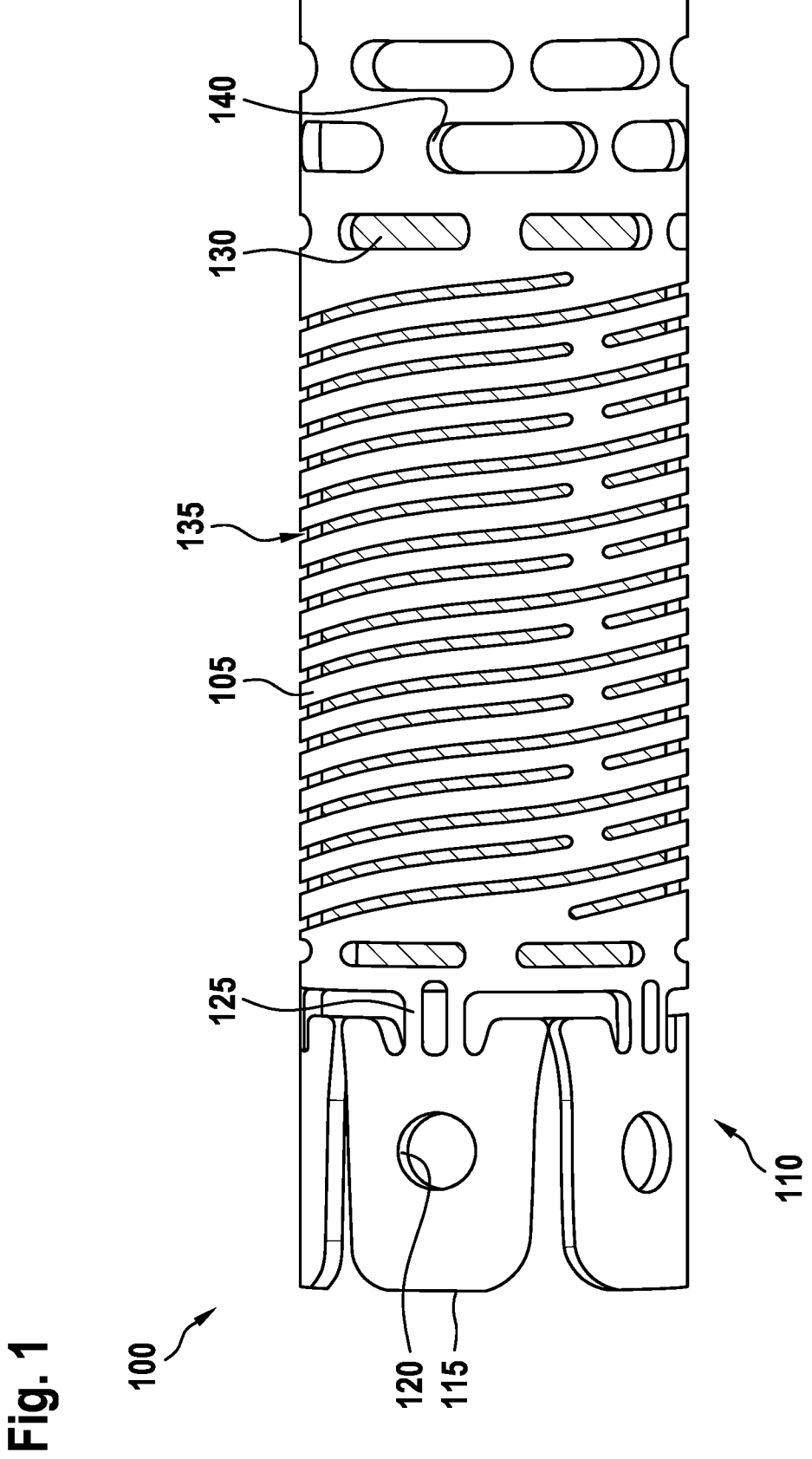

If the apparatus comprises the sleeve according to one embodiment, the clamping device can be configured to be transferred from the attachment state into the release state when the sleeve is removed or displaced. The release state can advantageously be effected particularly easily by retracting the sleeve that holds the clamping wing down. By retracting the sleeve, the clamping wing can, for example, flip open from a pretensioned state into the original state. If, according to one embodiment, the clamping wing is, for example, configured as a shape memory element, the release state can be brought about by means of a transformation temperature that is below human body temperature. Alternatively, the release state can, for example, also be actively brought about by a defined impulse, for example an electrically controllable mechanism. This can take place alternatively or in addition to flipping open the clamping wing by retracting the sleeve.

According to another embodiment, the clamping device can comprise a web, whereby the web is configured to form a neck between the main body and the at least one clamping wing, in particular whereby the web has a smaller width than the clamping wing. The web can, for example, be implemented between the main body and the at least one clamping wing as a connection between the clamping wing and the main body. The web can advantageously be configured such that the force for opening and closing the clamping device by flipping open and folding down the clamping wing is suitable for implantation. The wall thickness of the web can correspond to the wall thickness of the main body and/or the clamping wing, for example. The web can, for example, have a width that is reduced relative to the circumferential direction and the circumference of the main body. The cross-sectional area of the web can be a third of the cross-sectional area of the clamping wing, for example. The web can also comprise a recess, for example to change the stiffness. If, according to one embodiment, the clamping device comprises a plurality of clamping wings, for example, the clamping device can have a web for each clamping wing.

According to one embodiment, the apparatus can advantageously be formed in one piece. The apparatus can be made of one material, for example a tube. This is advantageous for a compact design, since the apparatus as a one-piece structure requires little installation space. The apparatus can be cut from a tube, for example, and the at least one clamping wing can, for example, be implemented with the aid of punching processes, laser cutting or machining. If the apparatus according to one embodiment further comprises recesses in the clamping wing and/or a web, these can be configured by removing material by means of one of the aforementioned processing methods.

According to one embodiment, the tube-shaped main body of the apparatus can be configured as a hollow cylinder, in particular for receiving a flexible hose. The configuration as a hollow cylinder can be advantageous with respect to the stiffness and strength of the apparatus, because the main body can serve to transmit force and torque from the insertion device via the apparatus to the cardiac support system. To this end, ensuring a certain degree of stiffness and strength in both axial and rotational directions can be advantageous. The configuration as a hollow cylinder also allows the apparatus to receive a flexible hose, for example a silicone hose, in order to change the flexibility of the apparatus and also the strength characteristics of the apparatus with the hose receptacles.

According to one embodiment, the main body can further comprise at least one stiffening recess. The at least one stiffening recess is configured to change the stiffness of the main body. The stiffening recess can be advantageous to still maintain sufficient stiffness for force transmission at a specific flexibility of the main body. The specific flexibility of the main body and thus of the apparatus can be advantageous, for example to enable implantation via the aortic arch. The stiffening recess can be spiral-shaped, for example. For advantageous flexibility, the main body can in particular comprise a plurality of stiffening recesses over at least half the length of the main body.

According to one embodiment, the clamping device can be disposed on an end portion of the main body and, on another end portion opposite to the clamping device, the main body can comprise at least one attachment recess for attaching the insertion device. This embodiment advantageously enables the use of the apparatus as a connecting element between the cardiac support system on the side of the clamping device and the insertion device on the opposite side, which is a particularly space-saving and easy-to-implement attachment option. The apparatus can advantageously further be configured to be used in combination with different cardiac support systems and different insertion devices, for example by varying the recesses for attaching the cardiac support system and/or the insertion device.

According to another advantageous embodiment, the apparatus can have a length of less than 50 millimeters, in particular less than 40 millimeters. Additionally or alternatively, the at least one clamping wing can be flipped open at least 0.5 millimeters in the release state. Due to a short rigid length of the connection of the cardiac support system to the apparatus, this embodiment can be advantageous with respect to the use of the apparatus in the context of minimally invasive implantation methods, in particular to enable implantation via the aortic arch.

A method for producing the apparatus according to an embodiment is presented as well. The method comprises at least one step of forming a tube-shaped main body and a clamping device having at least one clamping wing in order to produce the apparatus. The clamping device is configured to mechanically couple the cardiac support system to an insertion device in an attachment state and to release the cardiac support system from the insertion device by flipping open the at least one clamping wing in a release state.

This method can, for example, be implemented in software or hardware or in a mixed form of software and hardware in a control device, for example.

The approach presented here further creates a production apparatus that is configured to carry out, control and/or implement the step of the method presented here in corresponding devices.

A computer program product or computer program having program code which can be stored on a machine-readable carrier or storage medium such as a semiconductor memory, a hard drive memory, or optical memory and is used to carry out, implement, and/or control the steps of the method according to the embodiment described above is also advantageous, in particular if the program product or program is executed on a computer or a production apparatus.

Figure 2:
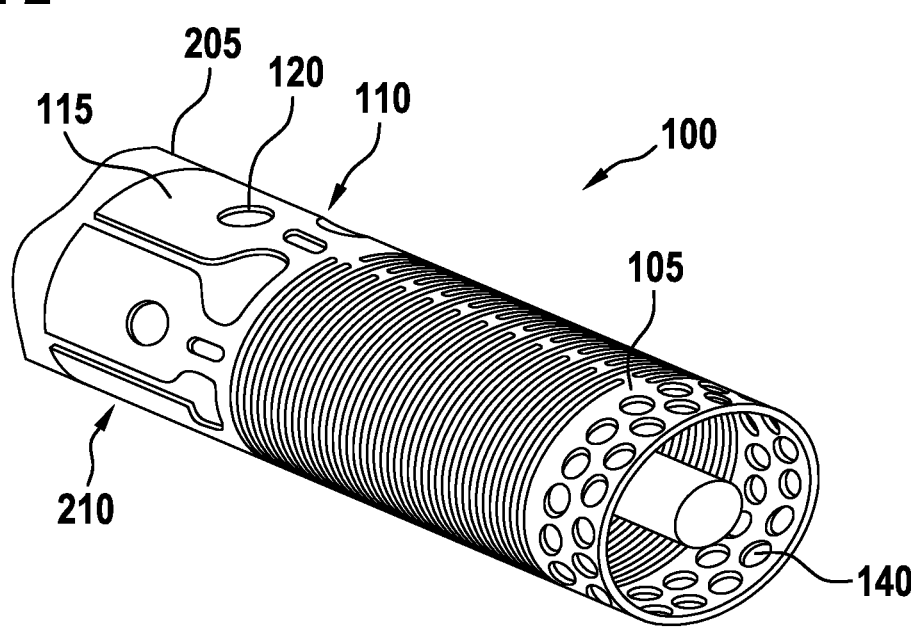
Figure 3:
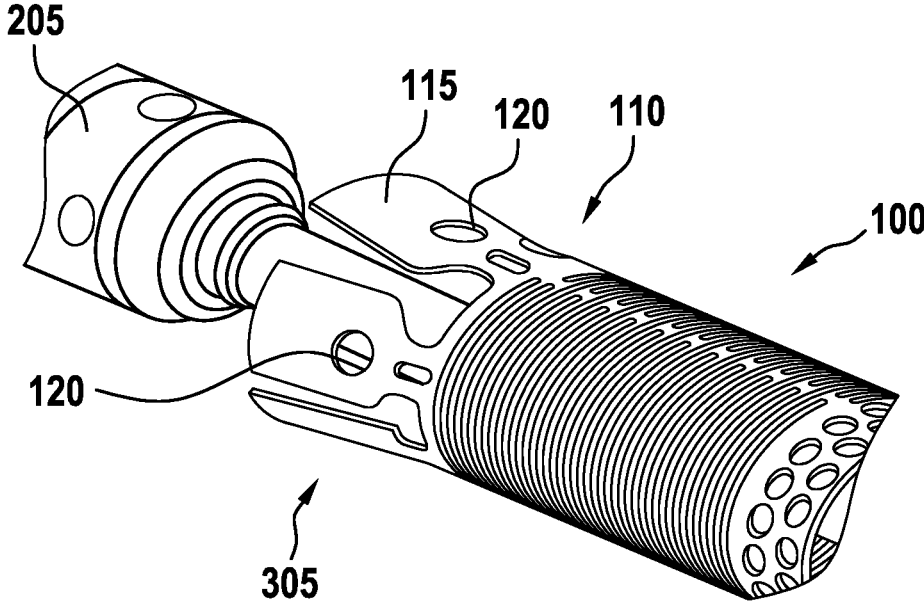
Figure 4A:
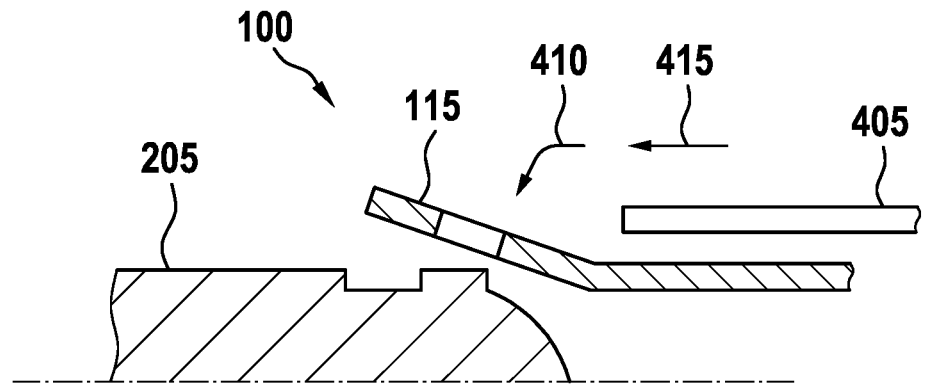
Figure 4B:
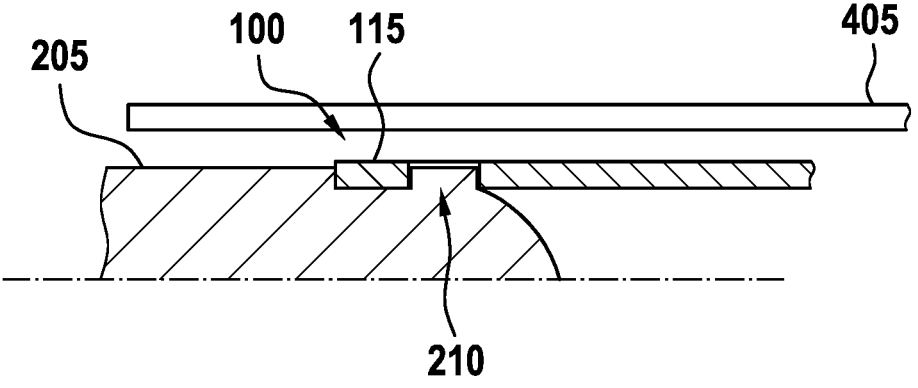
Figure 4C:
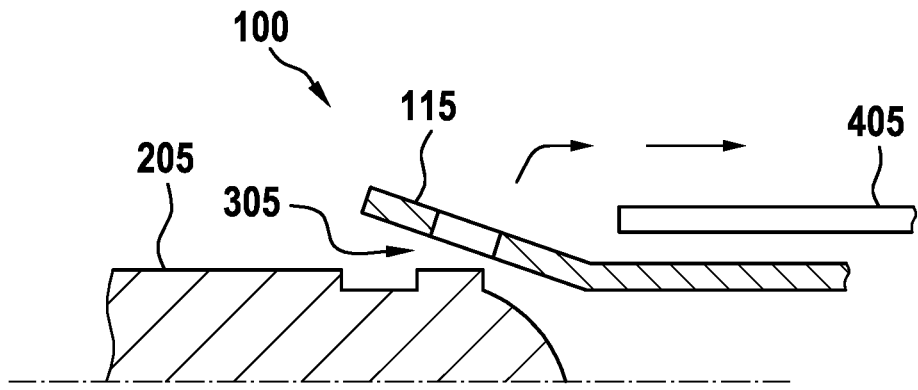
Figure 5:
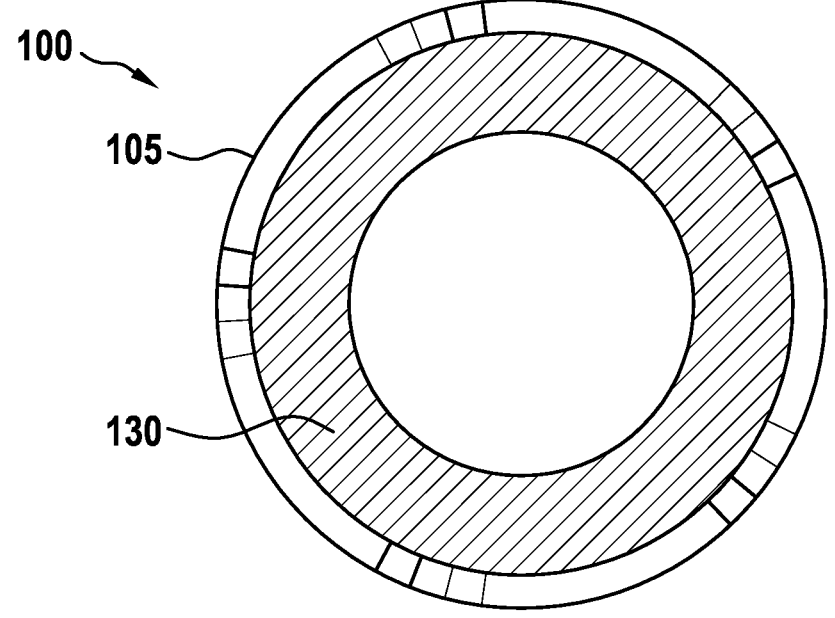

Design examples of the approach presented here are shown schematically in the drawings and explained in more detail in the following description. The figures show:

FIG. 1 a side view of a coupling apparatus for attaching a cardiac support system to an insertion device;

FIG. 2 a perspective illustration of the coupling apparatus in the attachment state;

FIG. 3 a perspective illustration of a release state of the coupling apparatus;

FIG. 4a to 4c partial sections of the coupling apparatus in various situations of releasable coupling;

FIG. 5 a cross-section of the coupling apparatus.

Figure 6:
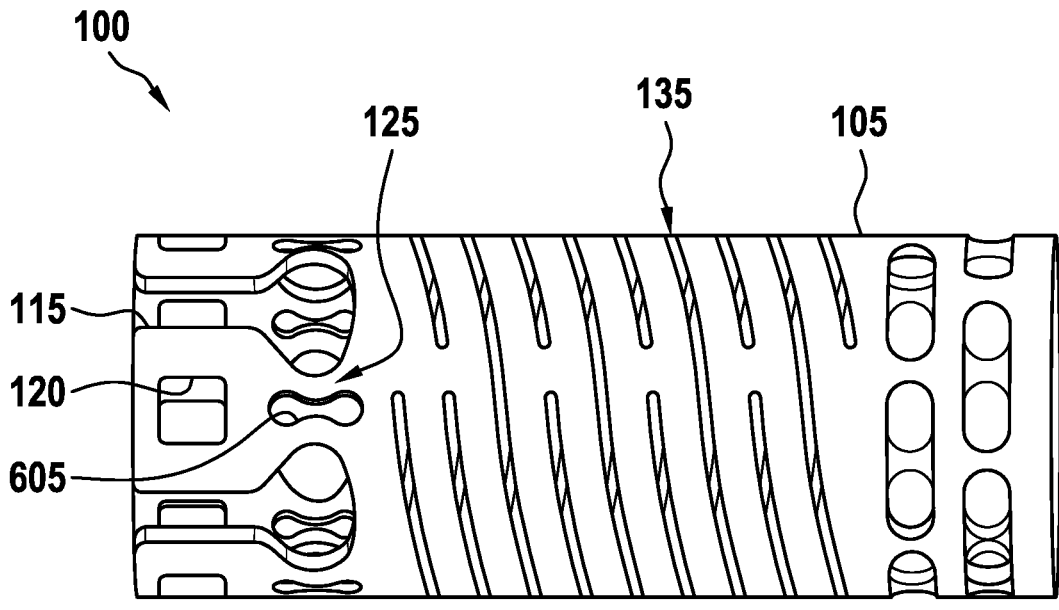

FIG. 6 a side view of the coupling apparatus in a further embodiment; and

Figure 7:
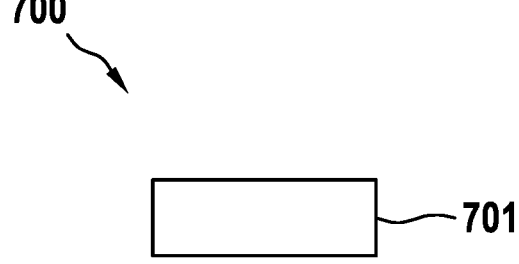

FIG. 7 a flow diagram of a method for producing an apparatus for attaching a cardiac support system to an insertion device according to one design example.

In the following description of favorable design examples of the present invention, the same or similar reference signs are used for the elements shown in the various figures, which have a similar effect, whereby a repeated description of these elements is omitted.

The apparatus 100 shown in FIG. 1 is configured to releasably couple a cardiac support system to an insertion device. For this purpose, the coupling apparatus 100 comprises a tube-shaped main body 105 and a clamping device 110 having at least one clamping wing 115. The clamping device 110 is configured to mechanically couple the cardiac support system to the insertion device in an attachment state and to release the cardiac support system from the insertion device by flipping open the at least one clamping wing 115 in a release state. The clamping device 110 here comprises three clamping wings 115, for example.

The clamping wings 115 can optionally be configured as a shape memory element. The clamping wings 115 can further comprise at least one element or, as shown here, at least one recess 120 for receiving an element for mechanically coupling the cardiac support system to the apparatus in a form-locking manner. The cardiac support system, for example the housing, or the apparatus 100 comprise elements or recesses that fit together in a form-locking manner. The element thickness or the height of the elements can preferably correspond to the wall thickness of the apparatus 100 so as not to affect the release of the cardiac support system; however the wall thickness can also be more or less. The element can, for example, be shaped like a circle, corresponding to the recess 120 in the clamping wing 115 shown here, or oval, or like a triangle, polygon or star. The cross-section of the element can also be shaped like a rectangle or semicircle, or include a flattened portion, a rounded portion, or an undercut.

According to one design example, the clamping device 110 can comprise at least two clamping wings 115. Optionally, the at least two clamping wings 115 are evenly spaced (for example on either side), as shown here.

The apparatus 100 here also comprises a web 125, whereby the web 125 is configured to form a neck between the main body 105 and the at least one clamping wing 115. In particular as in this design example, the web 125 can have a smaller width than the clamping wing. If the clamping device 110 comprises a plurality of clamping wings 115, each clamping wing 115 can be connected to the main body 105 via an associated web 125.

According to the design example shown here, the apparatus 100 is formed in one piece. The shape of the apparatus 100 can be cut from a tube, for example consisting of Nitinol (nickel-titanium alloy), and configured by means of punching processes, laser cutting or machining. The main body 105 can optionally be configured as a hollow cylinder, in particular for receiving a flexible hose 130, as shown in FIG. 1.

According to the design example shown here, the main body 105 comprises at least one stiffening recess 135. The at least one stiffening recess 135 is configured to change the stiffness of the main body 135. The at least one stiffening recess 135 can be configured by means of a suitable removal of material, for example in the form of a punching process, laser cutting or machining. Spiral-shaped recesses such as the stiffening recesses 135 shown here are particularly suitable as stiffening recesses 135 to still maintain sufficient stiffness for force transmission at a specific flexibility. The flexibility of the apparatus 100 and also the strength characteristics of the apparatus 100 can furthermore be influenced by the receptacle of the hose 130.

As shown here, the clamping device 110 can be disposed on an end portion of the main body 105. According to this design example, the main body 105 comprises at least one attachment recess 140 for attaching the insertion device on another end portion opposite to the clamping device 110. The attachment recess 140 can have an oval shape, as here, or be configured in one of the already described variants of the recess 120 of the clamping wing 115, whereby a component of the insertion device comprises the elements that fit in a form-locking manner in order to securely attach the insertion device to the apparatus 100. The attachment recess 140 can be produced by means of one of the aforementioned processing methods for removing material. As a structural element of the main body 105, the attachment recess 140 serves to transmit force and torque from the insertion device via the apparatus 100 to the cardiac support system. To this end, a certain degree of stiffness and strength in both axial and rotational directions should be ensured.

According to one design example, the apparatus 100 has a length of less than 50 millimeters, in particular a rigid length of less than 40 millimeters.

FIG. 2 shows a schematic illustration of an apparatus 100 for attaching a cardiac support system 205 to an insertion device according to one design example. The apparatus 100 is shown in the attachment state 210 of the clamping device 110 to the cardiac support system 205, whereby the other end portion of the main body 105 of the apparatus 100 opposite to the clamping device 110 comprises the attachment recesses 130, here having a circular shape, for attaching the insertion device to the apparatus 100. Only the portion of the cardiac support system 205 connected to the apparatus 100 and a component of the cardiac support system 205 passed through the cylindrical hollow body of the main body 105 of the apparatus 100 are shown as an example. The attachment state 210 is indicated by the folded-down state of the clamping wings 115 and the form-locking abutment of the recesses 120 of the clamping wings 115 on the form-locking elements provided on the cardiac support system 205. The apparatus 100 can be referred to here as a closed clamp.

FIG. 3 shows a further situation of the design example of the apparatus 100 shown in the preceding FIG. 2. The illustration shows the apparatus 100 as an open clamp, the clamping device 110 thus exhibits the release state 305 of the cardiac support system 205. The release state 305 is illustrated by the flipping open of the clamping wings 115. The apparatus 100 has a distance to the form-locking elements of the cardiac support system 205 on which the recess 120 of the clamping wings 115 rests in the closed state of the clamping wings, whereby the distance represents the release of the cardiac support system 205 by the flipping open of the clamping wings.

FIG. 4a to 4c show partial sections of an apparatus 100 for attaching a cardiac support system 205 to an insertion device according to one design example. Each figure shows a respective cross-sectional view of a situation of the releasable coupling of the cardiac support system 205 to the apparatus 100. According to the design examples shown in FIG. 4a to 4c, the apparatus 100 comprises a sleeve 405. The sleeve 405 is configured to enclose the apparatus 100 in the attachment state of the clamping device. In this case, the clamping device is optionally configured to be transferred from the attachment state 210 into the release state 305 when the sleeve 405 is removed. The sleeve 405 is shown here as a catheter. In the design example shown here, the at least one clamping wing 115 of the clamping device and a portion of the main body of the apparatus 100 is shown as part of the apparatus 100.

As a situation of the releasable coupling of the cardiac support system 205 to the apparatus 100, FIG. 4a shows the connecting of the cardiac support system 205 to the clamping wing 115 of the apparatus 100 and the loading of the cardiac support system 205 attached by means of the clamping wing 115 into the catheter as a sleeve 405. The figure shows how the attachment consisting of the housing of the cardiac support system 205 and the clamping wing 115 of the apparatus 100 is brought together with the catheter as a sleeve 405 of the apparatus 100. When attaching the cardiac support system 205 to the apparatus 100, the clamping wing 115 is pushed over a housing section of the cardiac support system 205 provided with a form-locking element. This is indicated here by the arrow 410. The sleeve 405 is then guided over the flexible and bendable clamping wing 115. This is indicated as an example here by the arrow 415. The clamping wing 115 engages the form-locking element of the housing of the cardiac support system 205 and is held down by the sleeve 405. The form-locking element and the corresponding recess of the clamping wing 115 and the housing of the cardiac support system 205 can be configured in a variety of geometric shapes, for example circular, oval, triangular or polygonal or star-shaped. The form-locking element can be provided on the housing of the cardiac support system 205 or on the clamping wing 115, whereby the counterpart then comprises the matching recess to the form-locking element.

FIG. 4b shows a situation of the attachment state 210 of the apparatus 100 to the cardiac support system 205. The clamping wing 115 is folded down in accordance with the attachment state 210; i.e. the clamping device is closed. In the attachment state 210, it is possible to insert and position the cardiac support system 205. The sleeve 405 in the form of the catheter is inserted into the circulatory system. During the insertion, implantation and positioning of the cardiac support system 205, axial and rotational force transmission to the cardiac support system 205 for control from the outside is possible by means of the apparatus 100. The attachment of the cardiac support system 205 to the apparatus 100 is implemented such that the clamping wing 115 remains securely held via the sleeve 405 by a radial force and connected to the housing of the cardiac support system 205. Advantageously, therefore, both forward and backward movements as well as rotational movements can be carried out during implantation without affecting the connection of the cardiac support system 205 to the apparatus 100.

FIG. 4c shows the release of the cardiac support system 205 by means of the apparatus 100 and the retraction of the sleeve 405 with the catheter as a situation of the releasable coupling of the cardiac support system 205 to the apparatus 100. The release, and thus the separation of the connection between the housing of the cardiac support system 205 and the apparatus 100, takes place by the controlled retraction of the sleeve 405 in the form of a catheter, for example by means of a control signal of a control device or mechanically via a handle, for example when the cardiac support system 205 is positioned at the destination. By retracting the sleeve 405 to release the cardiac support system 205, the clamping wing 115 flips open in order to bring about the release state 305. The clamping wing 115 goes from a pretensioned state, for example, back to the original state, in which the clamping wing 115 projects at a specific angle to the main body of the apparatus 100, i.e. is flipped open, for example by means of the shape memory of the clamping wing 115 according to one design example. When the form-locking element is provided on the housing of the cardiac support system 205, the flipped open height of the clamping wing 115 exceeds the height of the form-locking element. This releases the form-locking connection between the apparatus 100 and the housing of the cardiac support system 205, and the cardiac support system 205 can be uncoupled from the catheter by means of the apparatus 100. The separation process can either affect all of the elements at the same time or take place incrementally. The catheter can thus be withdrawn from the body, while the released cardiac support system 205 remains at the destination.

FIG. 5 shows a view onto the apparatus 100 in the axial direction of the main body 105 of the apparatus, i.e. a cross-section of the main body 105 of the apparatus 100. The apparatus 100 is configured here as a cylindrical hollow body. A flexible hose 130 in the form of a silicone hose is accommodated inside the main body 105 of the apparatus 100, which in this case, as an example, is a Nitinol tube, in order to improve the mechanical properties of the apparatus 100, which can be advantageous when inserting the cardiac support system into a blood vessel for implanting the cardiac support system, for example.

Compared to the design examples of the apparatus 100 shown in FIG. 1 to 3, the embodiment shown in FIG. 6 has a variation with respect to the shape of the recess 120 on the clamping wings 115. Here, the recess 120 on each clamping wing 115 has a square shape. The web 125, which is configured as a neck and thus respectively connects the clamping wing 115 to the main body 105, further comprises a web recess 605, whereby the web recess 605, like the stiffening recesses 135, can be implemented on the main body 105 to change the stiffness, and whereby the shape of the web 125 is configured such that the force for opening and closing the clamping wing 115 is suitable for implantation.

FIG. 7 shows a flow diagram of a method 700 for producing an apparatus for attaching a cardiac support system to an insertion device according to one design example. The method 700 comprises at least one step 701 of forming a tube-shaped main body and a clamping device having at least one clamping wing, whereby the clamping device is configured to mechanically couple a cardiac support system to an insertion device in an attachment state and to release the cardiac support system from the insertion device by flipping open the at least one clamping wing in a release state.

If a design example includes an "and/or" conjunction between a first feature and a second feature, this should be read to mean that the design example according to one embodiment comprises both the first feature and the second feature and, according to another embodiment, comprises either only the first feature or only the second feature.

The invention claimed is:

1. An apparatus configured to be releasably coupled to a cardiac support system, the apparatus comprising:
   a tube-shaped body having a first end, a second end opposite the first end, and a longitudinal axis extending between the first end and the second end; and
   at least one clamping wing extending from the second end of the tube-shaped body in a direction having at least an axial component directed away from the first end;

wherein:
   the at least one clamping wing is flexible or bendable relative to the tube-shaped body between a first position corresponding to a release state and a second position corresponding to an attachment state;
   the at least one clamping wing extends obliquely outward from the second end of the tube-shaped body relative to the longitudinal axis in the first position;
   the at least one clamping wing extends axially from the second end of the tube-shaped body relative to the longitudinal axis in the second position; and
   the apparatus is configured to be releasably coupled to the cardiac support system by applying a radial force onto the cardiac support system with the at least one clamping wing when the at least one clamping wing is in the attachment state.

2. The apparatus of claim 1, wherein the at least one clamping wing comprises a shape memory polymer or a shape memory alloy.

3. The apparatus of claim 1, wherein the at least one clamping wing comprises at least one protrusion configured to engage an end portion of the cardiac support system in a form-locking manner.

4. The apparatus of claim 1, wherein the at least one clamping wing comprises at least two clamping wings.

5. The apparatus of claim 4, wherein the at least two clamping wings are evenly spaced annularly about the second end of the tube-shaped body.

6. The apparatus of claim 1, further comprising a sleeve configured to at least partially enclose the apparatus when the at least one clamping wing is in the second position.

7. The apparatus of claim 6, wherein the at least one clamping wing is configured to transition between the attachment state and the release state when the sleeve is displaced.

8. The apparatus of claim 1, wherein the apparatus further comprises a web, wherein the web is configured to form a neck between the tube-shaped body and the at least one clamping wing.

9. The apparatus of claim 8, wherein a width of the web is smaller than a width of the at least one clamping wing.

10. The apparatus of claim 1, wherein the tube-shaped body and the at least one clamping wing are formed of one piece.

11. The apparatus of claim 1, wherein the tube-shaped body comprises a hollow cylinder configured to at least partially receive a flexible hose.

12. The apparatus of claim 1, wherein the tube-shaped body comprises at least one stiffening recess, wherein the at least one stiffening recess is configured to change a stiffness of the tube-shaped body.

13. The apparatus of claim 1, wherein the tube-shaped body comprises at least one attachment recess on the first end of the tube-shaped body opposite the second end.

14. The apparatus of claim 1, wherein the apparatus has a length of less than 50 millimeters.

15. The apparatus of claim 1, wherein the at least one clamping wing comprises at least one recess for receiving an end portion of the cardiac support system to mechanically couple the cardiac support system to the apparatus.

16. The apparatus of claim 1, wherein the cardiac support system is coaxial with the tube-shaped body in the attachment state.

17. The apparatus of claim 1, further comprising a sleeve configured to translate axially along a longitudinal axis of the apparatus, wherein the sleeve is configured to at least partially enclose the at least one clamping wing in the attachment state.

18. The apparatus of claim 17, wherein translating the sleeve proximally transitions the apparatus to the release state.

19. The apparatus of claim 1, wherein the at least one clamping wing is pretensioned to the second position.

20. The apparatus of claim 1, wherein the at least one clamping wing is configured to transition between the first position and the second position by flipping the at least one clamping wing relative to the tube-shaped body.

* * * * *